United States Patent
Chang

(10) Patent No.: US 8,535,674 B2
(45) Date of Patent: *Sep. 17, 2013

(54) TREATING BREAST CANCER AND INHIBITING CANCER-ASSOCIATED BONE LOSS WITH ANTI-IL-20 ANTIBODY

(75) Inventor: Ming-Shi Chang, Tainan (TW)

(73) Assignee: National Cheng Kung University, Tainan (TW)

( * ) Notice: Subject to any disclaimer, the term of this patent is extended or adjusted under 35 U.S.C. 154(b) by 407 days.

This patent is subject to a terminal disclaimer.

(21) Appl. No.: 12/815,855

(22) Filed: Jun. 15, 2010

(65) Prior Publication Data

US 2011/0305698 A1    Dec. 15, 2011

(51) Int. Cl.
*A61K 39/395* (2006.01)
(52) U.S. Cl.
USPC .................................... 424/145.1; 424/133.1
(58) Field of Classification Search
None
See application file for complete search history.

(56) References Cited

U.S. PATENT DOCUMENTS

| | | | |
|---|---|---|---|
| 7,189,394 B2 | 3/2007 | Thompson et al. | |
| 7,435,800 B2 | 10/2008 | Chang | |
| 7,611,705 B2 | 11/2009 | Chang | |
| 7,837,994 B2 | 11/2010 | Chang | |
| 8,012,478 B2 | 9/2011 | Chang | |
| 8,377,441 B2 * | 2/2013 | Chang | 424/133.1 |
| 2005/0170468 A1 | 8/2005 | Xu et al. | |
| 2008/0311115 A1 * | 12/2008 | Chang | 424/133.1 |
| 2009/0048432 A1 | 2/2009 | Chang | |
| 2011/0064731 A1 | 3/2011 | Chang | |

FOREIGN PATENT DOCUMENTS

EP    2050458 A1    4/2009

OTHER PUBLICATIONS

Balmana et al. Ann Oncol 2009; 20(supp 4):iv19-20.*
Kataja et al., Ann Oncol 2009; 20(sup 4): iv10-14.*
Nelson et al., Ann. Intern Med. 2009; 151:727-737.*
Fox et al, Breast Cancer Research, 2007; 9:216 pp. 1-11.*
Body et al., Clin Cancer Res 2006; 12:1221-28.*
Hsing et al., Cytokine, 2006; 35:44-52.*
Heuzé-Vourc'h et al., Biochem Biophys Res Commun, 2005; 333:470-475.*
Howe et al. Endocr Relat Cancer 2001; 8:97-114.*
Hsieh et al., Genes Immunity 2006; 7:234-42.*
Baird et al., Eur. J. Cancer 2011; 47:1908-18.*
Baselga, The EGFR as a target for anticancer therapy—focus on cetuximab. Eur J Cancer. Sep. 2001;37 Suppl 4:S16-22.
Holliger et al., "Diabodies": small bivalent and bispecific antibody fragments. Proc Natl Acad Sci U S A. Jul. 15, 1993;90(14):6444-8.
Hor et al., The T-cell lymphokine interleukin-26 targets epithelial cells through the interleukin-20 receptor 1 and interleukin-10 receptor 2 chains. J Biol Chem. Aug. 6, 2004;279(32):33343-51. Epub Jun. 3, 2004.
Williams et al., Tumor angiogenesis as a prognostic factor in oral cavity tumors. Am J Surg. Nov. 1994;168(5):373-80.
Zheng et al., Human interleukin 24 (MDA-7/IL-24) protein kills breast cancer cells via the IL-20 receptor and is antagonized by IL-10. Cancer Immunol Immunother. Feb. 2007;56(2):205-15. Epub May 19, 2006.
Jung et al., "Analysis of the expression profiles of cytokines and cytokine-related genes during the progression of breast cancer growth in mice", *Oncology Reports* 22:1141-1147, 2009.
Hsing et al., "The distribution of interleukin-19 in healthy and neoplastic tissue", *Cytokine* 44 (2008) 221-228.
Sakurai et al., "Expression of IL-19 and its receptors in RA: potential role for synovial hyperplasia formation", *Rheumatology* 2008;47:815-820.
Alanärä et al., "Expression of IL-10 family cytokines in rheumatoid arthritis: elevated levels of IL-19 in the joints", *Scand J Rheumatol* 2010;39:118-126.

\* cited by examiner

*Primary Examiner* — Sheela J Huff
*Assistant Examiner* — Jessica H Roark
(74) *Attorney, Agent, or Firm* — Wolf, Greenfield & Sacks, P.C.

(57) ABSTRACT

Use of an anti-IL-20 antibody, either alone or in combination with an anti-RANKL antibody, for treating breast cancer and inhibiting cancer-associated bone loss.

22 Claims, 2 Drawing Sheets

A.

B.

TREATING BREAST CANCER AND INHIBITING CANCER-ASSOCIATED BONE LOSS WITH ANTI-IL-20 ANTIBODY

BACKGROUND OF THE INVENTION

Breast cancer is the most common cancer in women worldwide. Breast cancer cells tend to metastasize from breast tissues to various other tissues/organs (e.g., brain, bone, and lung), thereby exacerbating the disease.

In addition to breast cancer, other cancers (e.g., prostate cancer, colon cancer, and lung cancer) can also result in bone metastases. Indeed, bone metastases are a major clinical concern that can cause severe bone loss, leading to rapid degradation in the quality of life for patients.

It is of great importance to develop a new method for treating breast cancer and suppressing cancer-associated bone loss.

SUMMARY OF THE INVENTION

In one aspect, the present invention features a method for treating breast cancer by administering to a subject in need thereof an effective amount of an anti-IL-20 antibody, optionally in combination with an anti-RANKL antibody (e.g., AMG 162). In one example, the subject is a breast cancer patient suffering from or at risk for bone metastasis or bone loss.

The anti-IL-20 antibody to be used in the method of this invention can be a naturally-occurring antibody, an antigen-binding fragment thereof, or a genetically engineered antibody (e.g., a humanized antibody, a chimeric antibody, or a single-chain antibody). It can contain a heavy chain variable region ($V_H$) including all of the complementarity-determining regions (CDRs) in the $V_H$ of monoclonal antibody mAb7E (SEQ ID NO:4) and a light chain variable region ($V_L$) including all of the CDRs in the $V_L$ of mAb7E (SEQ ID NO:8). In one example, it is an antibody containing SEQ ID NO:4 and SEQ ID NO:8 (e.g., mAb7E or an antigen-binding fragment thereof).

As used herein, the term "treating" refers to the application or administration of a composition including an anti-IL-20 antibody to a subject, who has breast cancer, a symptom of the cancer, or a predisposition toward the cancer, with the purpose to cure, heal, alleviate, relieve, alter, remedy, ameliorate, improve, or affect the disease, the symptoms of the disease, or the predisposition toward the disease. "An effective amount" as used herein refers to the amount of each active agent required to confer therapeutic effect on the subject, either alone or in combination with one or more other active agents. Effective amounts vary, as recognized by those skilled in the art, depending on route of administration, excipient choice, and co-usage with other active agents.

In another aspect, the present invention features a method for suppressing cancer-associated bone loss in a cancer patient using an effective amount of any of the anti-IL-20 antibodies described above, either alone or in combination with an anti-RANKL antibody. In one example, the cancer patient has breast cancer, prostate cancer, lung cancer, renal cell carcinoma, giant cell tumor of bone, or multiple myeloma with bone metastasis. In another example, the cancer patient has been subjected to a cancer treatment that causes bone loss.

Also within the scope of this invention is a pharmaceutical composition containing an anti-IL-20 antibody, and optionally, an anti-RANKL antibody, for use in treating breast cancer or suppressing cancer-associated bone loss, or for use in manufacturing a medicament for breast cancer treatment and bone loss suppression.

The details of one or more embodiments of the invention are set forth in the description below. Other features or advantages of the present invention will be apparent from the following drawings and detailed description of several examples, and also from the appended claims.

BRIEF DESCRIPTION OF THE DRAWINGS

The drawings are first described.

DETAILED DESCRIPTION OF THE INVENTION

Figure 1:
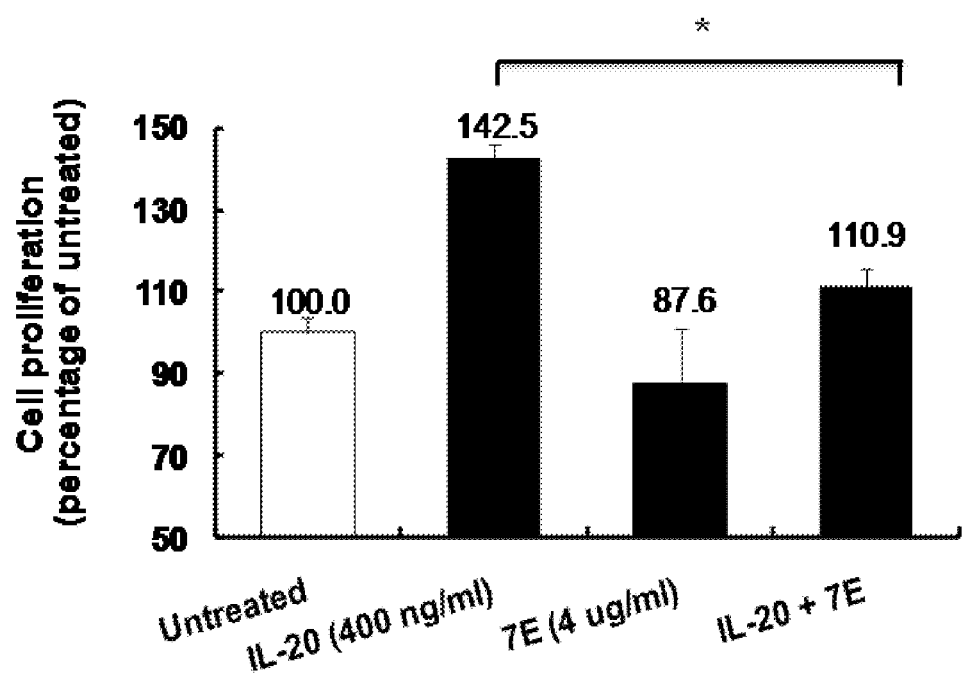
FIG. 1 is a chart showing growth inhibition of 4T1 breast cancer cells with anti-IL-20 antibody mAb7E in the presence or absence of IL-20. Values shown in this figure refer to mean±SD. *: $P<0.05$ (compared with IL-20 treatment).

Disclosed herein is a method for treating breast cancer or suppressing cancer-associated bone loss with an anti-IL-20 antibody, and optionally, an anti-RANKL antibody. An anti-IL-20 or anti-RANKL antibody is a naturally-occurring antibody, an antigen-binding fragment thereof, or a genetically engineered antibody that neutralizes IL-20 or RANKL, i.e., binding to either antigen and blocking the IL-20-mediated or RANKL-mediated signaling pathway.

Naturally-occurring anti-IL-20 and anti-RANKL antibodies, either polyclonal or monoclonal, can be prepared by conventional methods, using an IL-20 protein, an RANKL protein, or a fragment thereof. See, e.g., Harlow and Lane, (1988) Antibodies: A Laboratory Manual, Cold Spring Harbor Laboratory, New York. A "monoclonal antibody" refers to a homogenous antibody population and a "polyclonal antibody" refers to a heterogenous antibody population. These two terms do not limit the source of an antibody or the manner in which it is made.

IL-20 is a member of the IL-10 cytokine family. Human IL-20 is described under GenBank Accession Number NP_061194 (protein) and NM_018724 (gene). RANKL (Receptor Activator for Nuclear Factor κ B Ligand), also known as TNF-related activation-induced cytokine (TRANCE), osteoprotegerin ligand (OPGL), and ODF (osteoclast differentiation factor), is a protein molecule important in bone metabolism. Human RANKL is described under GenBank Accession Number AAB86811 (protein) and AF019047 (gene).

To produce antibodies against IL-20 or RANKL, the protein or a fragment thereof can be coupled to a carrier protein, such as KLH, mixed with an adjuvant, and injected into a host animal. Antibodies produced in the animal can then be purified by a protein A column and/or IL-20/IL-20 peptide or RANKL/RANKL peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and Corynebacterium parvum.

Polyclonal antibodies are present in the sera of the immunized subjects. Monoclonal antibodies can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production. After obtaining antibodies specific to IL-20, their ability to neutralize IL-20 can be determined by a routine procedure.

Fully human anti-IL-20 and anti-RANKL antibodies, such as those expressed in transgenic animals are also features of the invention. See, e.g., Green et al., Nature Genetics 7:13 (1994), and U.S. Pat. Nos. 5,545,806 and 5,569,825.

Antigen-binding fragments (e.g., F(ab')$_2$, Fab, or Fv) of naturally-occurring anti-IL-20/anti-RANKL antibodies can be generated by known techniques. For example, F(ab')$_2$ fragments can be produced by pepsin digestion of an antibody molecule and Fab fragments can be generated by reducing the disulfide bridges of F(ab')$_2$ fragments.

The anti-IL-20 antibody or anti-RANKL antibody to be used in this invention can also be a genetically engineered antibody, e.g., a humanized antibody, a chimeric antibody, a single chain antibody (scFv), or a domain antibody (dAb; see Ward, et. Al., 1989, Nature, 341:544-546).

A humanized antibody contains a human immunoglobulin (i.e., recipient antibody) in which regions/residues responsible for antigen binding (i.e., the CDRs, particularly the specific-determining residues therein) are replaced with those from a non-human immunoglobulin (i.e., donor antibody). In some instances, one or more residues inside a frame region of the recipient antibody are also replaced with those from the donor antibody. A humanized antibody may also contain residues from neither the recipient antibody nor the donor antibody. These residues are included to further refine and optimize antibody performance. Antibodies can also be humanized by methods known in the art, e.g., recombinant technology.

A chimeric antibody is a molecule in which different portions are derived from different animal species, such as those having a variable region derived from a murine monoclonal antibody and a human immunoglobulin constant region. Such an antibody can be prepared via routine techniques described in, e.g., Morrison et al. (1984) Proc. Natl. Acad. Sci. USA 81, 6851; Neuberger et al. (1984) Nature 312, 604; and Takeda et al. (1984) Nature 314:452.

A single-chain antibody can be prepared via recombinant technology by linking a nucleotide sequence coding for a $V_H$ chain and a nucleotide sequence coding for a $V_L$ chain. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to IL-20/RANKL can be identified from the library following routine procedures. Positive clones can be subjected to further screening to identify those that suppress IL-20 or RANKL activity.

In one example, the anti-IL-20 antibody is monoclonal antibody mAb7E or a functional variant thereof. mAb7E is produced by the hybridoma cell line deposited at the American Type Culture Collection, 10801 Univer shy Boulevard, Manassas, Va. 20110-2209, U.S.A. and assigned a deposit number PTA-8687. See U.S. Pat. No. 7,435,800 and US 20090048432. This hybridoma cell line will be released to the public irrevocably and without restriction/condition upon granting a US patent on this application, and will be maintained in the ATCC for a period of at least 30 years from the date of the deposit for the enforceable life of the patent or for a period of 5 years after the date of the most recent. The amino acid sequences/cDNA sequences of the heavy and light chains of mAb7E are shown below.

```
Nucleotide sequence (SEQ ID NO: 1) and amino acid sequence
(SEQ ID NO: 2) of mAb 7E heavy chain
atg tac ttg gga ctg aac tat gta ttc ata gtt ttt ctc tta aat
 M   Y   L   G   L   N   Y   V   F   I   V   F   L   L   N          15 ggt gtc cag agt gaa ttg aag ctt gag gag tct gga gga ggc ttg
 G   V   Q   S   E   L   K   L   E   E   S   G   G   G   L          30 gtg cag cct gga gga tcc atg aaa ctc tct tgt gct gcc tct gga
 V   Q   P   G   G   S   M   K   L   S   C   A   A   S   G          45 ttc act ttt agt gac gcc tgg atg gac tgg gtc cgc cag tct cca
 F   T   F   S   D   A   W   M   D   W   V   R   Q   S   P          60 gag aag ggg ctt gag tgg att gct gaa att aga agc aaa gct aat
 E   K   G   L   E   W   I   A   E   I   R   S   K   A   N          75
```

-continued

```
aat tat gca aca tac ttt gct gag tct gtg aaa ggg agg ttc acc
 N   Y   A   T   Y   F   A   E   S   V   K   G   R   F   T          90 atc tca aga gat gat tcc aaa agt ggt gtc tac ctg caa atg aac
 I   S   R   D   D   S   K   S   G   V   Y   L   Q   M   N         105 aac tta aga gct gag gac act ggc att tat ttc tgt acc aag tta
 N   L   R   A   E   D   T   G   I   Y   F   C   T   K   L         120 tca cta cgt tac tgg ttc ttc gat gtc tgg ggc gca ggg acc acg
 S   L   R   Y   W   F   F   D   V   W   G   A   G   T   T         135 gtc acc gtc tcc tca gcc aaa acg aca ccc cca tct gtc tat cca
 V   T   V   S   S   A   K   T   T   P   P   S   V   Y   P         150 ctg gcc cct gga tct gct gcc caa act aac tcc atg gtg acc ctg
 L   A   P   G   S   A   A   Q   T   N   S   M   V   T   L         165 gga tgc ctg gtc aag ggc tat ttc cct gag cca gtg aca gtg acc
 G   C   L   V   K   G   Y   F   P   E   P   V   T   V   T         180 tgg aac tct gga tcc ctg tcc agc ggt gtg cac acc ttc cca gct
 W   N   S   G   S   L   S   S   G   V   H   T   F   P   A         195 gtc ctg cag tct gac ctc tac act ctg agc agc tca gtg act gtc
 V   L   Q   S   D   L   Y   T   L   S   S   S   V   T   V         210 ccc tcc agc acc tgg ccc agc gag acc gtc acc tgc aac gtt gcc
 P   S   S   T   W   P   S   E   T   V   T   C   N   V   A         225 cac ccg gcc agc agc acc aag gtg gac aag aaa att gtg ccc agg
 H   P   A   S   S   T   K   V   D   K   K   I   V   P   R         240 gat tgt ggt tgt aag cct tgc ata tgt aca gtc cca gaa gta tca
 D   C   G   C   K   P   C   I   C   T   V   P   E   V   S         255 tct gtc ttc atc ttc ccc cca aag ccc aag gat gtg ctc acc att
 S   V   F   I   F   P   P   K   P   K   D   V   L   T   I         270 act ctg act cct aag gtc acg tgt gtt gtg gta gac atc agc aag
 T   L   T   P   K   V   T   C   V   V   V   D   I   S   K         285 gat gat ccc gag gtc cag ttc agc tgg ttt gta gat gat gtg gag
 D   D   P   E   V   Q   F   S   W   F   V   D   D   V   E         300 gtg cac aca gct cag acg caa ccc cgg gag gag cag ttc aac agc
 V   H   T   A   Q   T   Q   P   R   E   E   Q   F   N   S         315 act ttc cgc tca gtc agt gaa ctt ccc atc atg cac cag gac tgg
 T   F   R   S   V   S   E   L   P   I   M   H   Q   D   W         330 ctc aat ggc aag gag ttc aaa tgc agg gtc aac agt gca gct ttc
 L   N   G   K   E   F   K   C   R   V   N   S   A   A   F         345 cct gcc ccc atc gag aaa acc atc tcc aaa acc aaa ggc aga ccg
 P   A   P   I   E   K   T   I   S   K   T   K   G   R   P         360 aag gct cca cag gtg tac acc att cca cct ccc aag gag cag atg
 K   A   P   Q   V   Y   T   I   P   P   P   K   E   Q   M         375 gcc aag gat aaa gtc agt ctg acc tgc atg ata aca gac ttc ttc
 A   K   D   K   V   S   L   T   C   M   I   T   D   F   F         390 cct gaa gac att act gtg gag tgg cag tgg aat ggg cag cca gcg
 P   E   D   I   T   V   E   W   Q   W   N   G   Q   P   A         405 gag aac tac aag aac act cag ccc atc atg gac aca gat ggc tct
 E   N   Y   K   N   T   Q   P   I   M   D   T   D   G   S         420 tac ttc gtc tac agc aag ctc aat gtg cag aag agc aac tgg gag
 Y   F   V   Y   S   K   L   N   V   Q   K   S   N   W   E         435 gca gga aat act ttc acc tgc tct gtg tta cat gag ggc ctg cac
 A   G   N   T   F   T   C   S   V   L   H   E   G   L   H         450 aac cac cat act gag aag agc ctc tcc cac tct cct ggt aaa TGA
 N   H   H   T   E   K   S   L   S   H   S   P   G   K   -         464
```

The bold-faced region refers to the $V_H$ of mAb 7E heavy chain (DNA sequence SEQ ID NO:3; protein sequence SEQ ID NO:4)

```
Nucleotide sequence (SEQ ID NO: 5) and amino acid sequence
(SEQ ID NO: 6) of mAb 7E light chain
atg atg agt cct gcc cag ttc ctg ttt ctg tta gtg ctc tgg att
 M   M   S   P   A   Q   F   L   F   L   L   V   L   W   I      15 cgg gaa acc aac ggt gat ttt gtg atg acc cag act cca ctc act
 R   E   T   N   G   D   F   V   M   T   Q   T   P   L   T      30 ttg tcg gtt acc att gga caa cca gcc tcc atc tct tgc aag tca
 L   S   V   T   I   G   Q   P   A   S   I   S   C   K   S      45 agt cag agc ctc ttg gat agt gat gga aag aca tat ttg aat tgg
 S   Q   S   L   L   D   S   D   G   K   T   Y   L   N   W      60 ttg tta cag agg cca ggc cag tct cca aag cac ctc atc tat ctg
 L   L   Q   R   P   G   Q   S   P   K   H   L   I   Y   L      75 gtg tct aaa ctg gac tct gga gtc cct gac agg ttc act ggc agt
 V   S   K   L   D   S   G   V   P   D   R   F   T   G   S      90 gga tca ggg acc gat ttc aca ctg aga atc agc aga gtg gag gct
 G   S   G   T   D   F   T   L   R   I   S   R   V   E   A     105 gag gat ttg gga gtt tat tat tgc tgg caa agt aca cat ttt ccg
 E   D   L   G   V   Y   Y   C   W   Q   S   T   H   F   P     120 tgg acg ttc ggt gga ggc acc aag ctg gaa atc aaa cgg gct gat
 W   T   F   G   G   G   T   K   L   E   I   K   R   A   D     135 gct gca cca act gta tcc atc ttc cca cca tcc agt gag cag tta
 A   A   P   T   V   S   I   F   P   P   S   S   E   Q   L     150 aca tct gga ggt gcc tca gtc gtg tgc ttc ttg aac aac ttc tac
 T   S   G   G   A   S   V   V   C   F   L   N   N   F   Y     175 aag tgg aag att gat ggc agt gaa cga caa aat ggc gtc ctg aac
 P   K   D   I   N   V   K   W   K   I   D   G   S   E   R     180 agt tgg act gat cag ccc aaa gac atc aat gtc gac agc aaa gac
 Q   N   G   V   L   N   S   W   T   D   Q   D   S   K   D     195 agc acc tac agc atg agc agc acc ctc acg ttg acc aag gac gag
 S   T   Y   S   M   S   S   T   L   T   L   T   K   D   E     210 tat gaa cga cat aac agc tat acc tgt gag gcc act cac aag aca
 Y   E   R   H   N   S   Y   T   C   E   A   T   H   K   T     225 tca act tca ccc att gtc aag agc ttc aac agg aat gag tgt tag
 S   T   S   P   I   V   K   S   F   N   R   N   E   C   -     239
```

The bold-faced region refers to the $V_L$ of mAb 7E light chain (DNA sequence SEQ ID NO:7; protein sequence SEQ ID NO:8).

A functional variant of mAb7E contains a $V_H$ at least 75% (80%, 85%, 90%, or 95%) identical to that of mAb7E (SEQ ID NO:4) and a $V_L$ at least 75% (80%, 85%, 90%, or 95%) identical to that of mAb7E (SEQ ID NO:8). As used herein, "percent homology" of two amino acid sequences is determined using the algorism described in Karlin and Altschul, Proc, Natl. Acad. Sci. USA 87:2264-2268, 1990, modified as described in Karlin and Altschul, Proc, Natl. Acad. Sci. USA 5873-5877, 1993. Such an algorism is incorporated into the NBLAST and XBLAST programs of Altschul et al., J. Mol. Biol. 215:403-410, 1990. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., Nucleic Acids Res. 25:3389-3402, 1997. When utilizing the BLAST and Gapped BLAST programs, the default parameters of the respective programs (e.g., XBLAST and NBLAST) are used. See www.ncbi.nlm.nih.gov.

A functional variant of mAb7E (e.g., a humanized antibody) can be generated by introducing mutations in a frame region (FR) of either the $V_H$ or $V_L$ of mAb7E and keep their CDRs intact. It is well known that CDRs of an antibody determine its specificity. Accordingly, mutations in FRs normally would not affect antibody specificity. The CDRs and FRs of an antibody can be determined based on the amino acid sequences of its $V_H$ and $V_L$. See www.bioinf.org.uk/abs. The binding-specificity of the functional equivalents described herein can be examined using methods known in the art, e.g., ELISA or western-blot analysis.

Alternatively, a functional variant of mAb7E is a genetically engineered antibody containing the same $V_H$ and $V_L$ as mAb7E. Such a variant (e.g., a chimeric antibody or a single-chain antibody) can be prepared following methods described above.

When used for treating breast cancer, any of the anti-IL-20 antibodies described herein can be mixed with a pharmaceutically acceptable carrier, either alone or in combination with an anti-RANKL antibody (e.g., AMG 162), to form a pharmaceutical composition. "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

The above-described pharmaceutical composition can be administered via a conventional route, e.g., orally, parenterally, by inhalation spray, topically, rectally, nasally, buccally, vaginally or via an implanted reservoir, to treat breast cancer or suppressing bone loss in a cancer patient who suffers from bone metastasis. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bio-availability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation.

In addition, the pharmaceutical composition described above can be administered to the subject via injectable depot routes of administration such as using 1-, 3-, or 6-month depot injectable or biodegradable materials and methods.

The anti-IL-20 antibody described herein, optionally in combination with an anti-RANKL antibody, is particularly effective in treating breast cancer with bone metastasis and in reducing cancer-associated bone loss, i.e., bone loss induced by a cancer with bone metastasis or by a cancer treatment that causes bone loss. Cancers that can metastasize to the bone include, but are not limited to, breast cancer, prostate cancer, lung cancer, colon cancer, renal cell carcinoma, giant cell tumor of bone, and multiple myeloma. Thus, a patient suffering from any of these cancers can be first examined via routine procedures to determine occurrence of bone metastasis or bone loss before being treated with the anti-IL-20 antibody or its combination with an anti-RANKL antibody.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Inhibiting Breast Cancer Cell Growth with mAb7E

Mouse 4T1 cells ($1 \times 10^4$) were cultured in DMEM supplemented with 10% FBS for 16 hours. The cells were then treated with (a) IL-20 (400 ng/ml), (b) mAb7E (4 µg/ml), or (c) a combination of IL-20 (400 ng/ml) and mAb7E (4 µg/ml) for 72 hours in DMEM supplemented with 1% FBS. After the treatment, the cells were incubated for 3 hours in the presence of 1 mg/ml MTT (Sigma-Aldrich, St. Louis, Mo.). The cells were then mixed with DMSO (Sigma-Aldrich) and their optical densities at 550 nm ($OD_{550}$) were determined.

As shown in FIG. 1, IL-20 stimulated 4T1 cell growth and this stimulatory effect was reversed by anti-IL-20 antibody mAb7E. In addition, antibody mAb7E also inhibited 4T1 cell growth in the absence of IL-20.

EXAMPLE 2

Treating Breast Cancer with mAb7E

Mouse breast cancer 4T1 cells, cultured under routine conditions, were suspended in PBS at a concentration of $1 \times 10^5$/100 µL. The cells were then injected directly into the left ventricle of 6-wk-old female BALB/c mice, which were anesthetized with pentobarbital (Sigma-Aldrich) at 50 mg/kg body weight via i.p., using an insulin syringe (29 gauge, BD Ultra-Fine; Becton Dickinson). After injection, the mice were randomly assigned into 3 groups (n=6/group), each treated by i.p. as follows:

Group 1: treated with PBS as a vehicle control three time in one week

Group 2: treated with a control mouse IgG (mIgG) at 4 mg/kg three times in one week Group 3: treated with mAb7E at 4 mg/kg three times in one week.

Mice not injected with 4T1 cancer cells were used as healthy controls. The survival rates of the three groups and the healthy controls were monitored on a daily basis until the end of the experiment.

Figure 2:
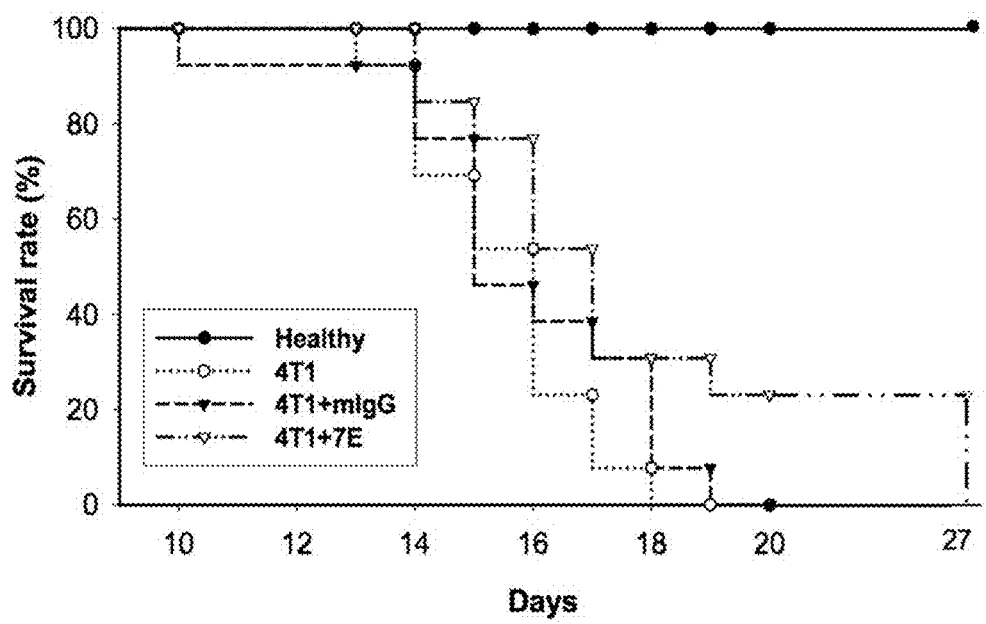
FIG. 2 is a diagram showing the effect of mAb7E in treating breast cancer. A: survival rates of healthy control mice, breast cancer cell (4T1)-injected mice, 4T1-injected mice treated with a control mouse IgG, and 4T1-injected mice treated with mAb7E. B: bone mineral densities of healthy control mice, 4T1-injected mice, 4T1-injected mice treated with a control mouse IgG, and 4T1-injected mice treated with mAb7E.
Figure 2:
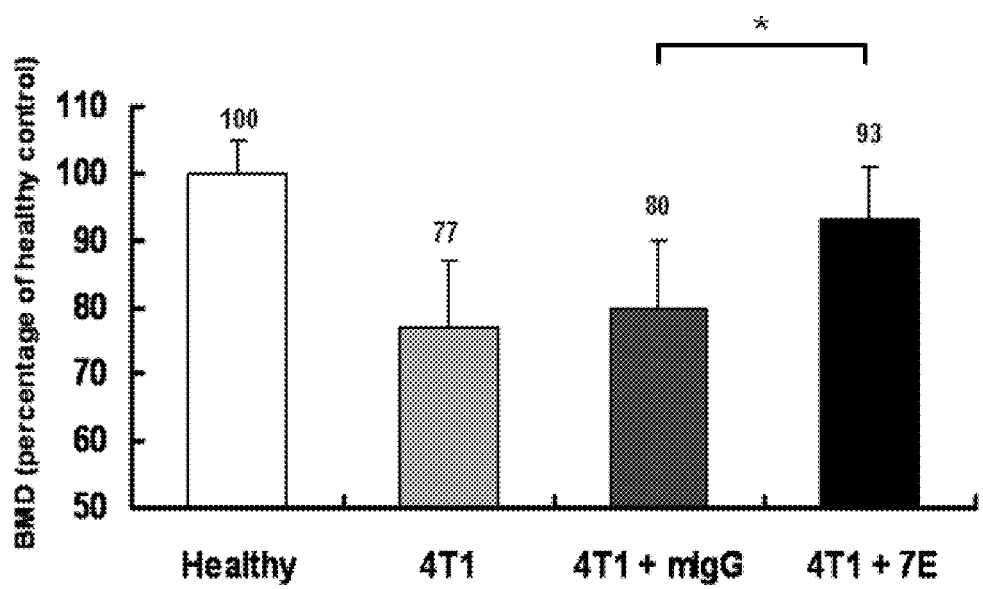

As shown in FIG. 2, panel A, the survival rate of the group 3 mice, treated with mAb7E, was much higher than that of the group 1 or group 2 mice, treating with the vehicle control or a control IgG, respectively.

Eighteen days post treatment, the tibia metaphyses of the mice were analyzed in-vivo on a micro-CT (1076; SkyScan) with a high resolution, low-dose X-ray scanner. Bone mineral density (BMD), a three-dimensional bone characteristic parameter, was analyzed in 50 consecutive slices. The results thus obtained were shown in FIG. 2, panel B. The Y axis values were calculated by the formula: (BMD of treated mice/BMD of healthy controls) %. The BMD of the mice injected with 4T1 cancer cells were reduced as compared to that of healthy control mice. This cancer-induced BMD was rescued significantly by mAb7E.

In an alternative study, $1 \times 10^5$ 4T1 cells (0.2 ml) were slowly injected into the bone marrow cavity of tibia in BALB/c mice. These mice were then treated with (a) PBS as a vehicle control, (b) a control mouse IgG (mIgG), or (c) mAb7E (4 mg/kg) via i.p. three times in one week. In the mice treated with PBS, tumor mass was observed around the proximal tibia 25 days after 4T1 injection. Twenty-eight days post treatment, the tibia metaphyses and bone mineral densities in all treated mice were examined following the methods described above. The results thus obtained indicate that mAb7E significantly rescued bone loss caused by breast cancer cells ($P<0.05$, as compared with mice treated with mIgG).

Taken together, the results obtained from this study clearly indicate that mAb7E improved survival rates of mice transplanted with breast cancer cells and suppressed bone loss induced by cancer cells.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating breast cancer, comprising administering to a subject in need thereof an effective amount of an anti-IL-20 antibody, wherein the subject is a breast cancer patient.

2. The method of claim 1, wherein the anti-IL-20 antibody is a humanized antibody, a chimeric antibody, a single-chain antibody, a monoclonal antibody or an antigen-binding fragment thereof.

3. The method of claim 2, wherein the anti-IL-20 antibody contains a heavy chain variable region and a light chain variable, wherein the complementarity determining regions of the heavy chain variable region are identical to those in SEQ ID NO:4 and the complementarity determining regions of the light chain variable region are identical to those in SEQ ID NO:8.

4. The method of claim 3, wherein the anti-IL-20 antibody comprises a heavy chain variable region set forth as SEQ ID NO:4 and a light chain variable region set forth as SEQ ID NO:8.

5. The method of claim 4, wherein the anti-IL-20 antibody is a chimeric antibody or a single-chain antibody.

6. The method of claim 4, wherein the anti-IL-20 antibody is monoclonal antibody mAb7E or an antigen-binding fragment thereof.

7. The method of claim 1, wherein the subject is a breast cancer patient suffering from or at risk for bone metastasis or cancer-induced bone loss.

8. The method of claim 7, wherein the anti-IL-20 antibody is a humanized antibody, a chimeric antibody, a single-chain antibody, a monoclonal antibody or an antigen-binding fragment thereof.

9. The method of claim 8, wherein the anti-IL-20 antibody contains a heavy chain variable region and a light chain variable region, wherein the complementarity determining regions of the heavy chain variable region are identical to those in SEQ ID NO:4 and the complementarity determining regions of the light chain variable region are identical to those in SEQ ID NO:8.

10. The method of claim 9, wherein the anti-IL-20 antibody comprises a heavy chain variable region set forth as SEQ ID NO:4 and a light chain variable region set forth as SEQ ID NO:8.

11. The method of claim 10, wherein the anti-IL-20 antibody is a chimeric antibody or a single-chain antibody.

12. The method of claim 10, wherein the anti-IL-20 antibody is monoclonal antibody mAb7E or an antigen-binding fragment thereof.

13. The method of claim 7, wherein the subject is co-administered with an anti-RANKL antibody.

14. A method for suppressing bone loss associated with cancer, the method comprising administering to a cancer patient in need thereof an effective amount of an anti-IL-20 antibody.

15. The method of claim 14, wherein the cancer patient has breast cancer, prostate cancer, colon cancer, lung cancer, renal cell carcinoma, giant cell tumor of bone, or multiple myeloma.

16. The method of claim 15, wherein the cancer patient suffers from bone metastasis.

17. The method of claim 14, wherein the anti-IL-20 antibody is a humanized antibody, a chimeric antibody, a single-chain antibody, a monoclonal antibody or an antigen-binding fragment thereof.

18. The method of claim 17, wherein the anti-IL-20 antibody contains a heavy chain variable region and a light chain variable region, wherein the complementarity determining regions of the heavy chain variable region are identical to those in SEQ ID NO:4 and the complementarity determining regions of the light chain variable region are identical to those in SEQ ID NO:8.

19. The method of claim 18, wherein the anti-IL-20 antibody comprises a heavy chain variable region set forth as SEQ ID NO:4 and a light chain variable region set forth as SEQ ID NO:8.

20. The method of claim 19, wherein the anti-IL-20 antibody is a chimeric antibody or a single-chain antibody.

21. The method of claim 19, wherein the anti-IL-20 antibody is monoclonal antibody mAb7E or an antigen-binding fragment thereof.

22. The method of claim 14, further comprising administering to the cancer patient an effective amount of an anti-RANKL antibody.

* * * * *

SEQUENCE LISTING

```
<160> NUMBER OF SEQ ID NOS: 8

<210> SEQ ID NO 1
<211> LENGTH: 1395
<212> TYPE: DNA
<213> ORGANISM: Mus musculus

<400> SEQUENCE: 1
atgtacttgg gactgaacta tgtattcata gttttctct  taaatggtgt  ccagagtgaa        60
ttgaagcttg aggagtctgg aggaggcttg gtgcagcctg gaggatccat  gaaactctct       120
tgtgctgcct ctggattcac ttttagtgac gcctggatgg actgggtccg  ccagtctcca       180
gagaaggggc ttgagtggat tgctgaaatt agaagcaaag ctaataatta  tgcaacatac       240
tttgctgagt ctgtgaaagg gaggttcacc atctcaagag atgattccaa  aagtggtgtc       300
tacctgcaaa tgaacaactt aagagctgag gacactggca tttatttctg  taccaagtta       360
tcactacgtt actggttctt cgatgtctgg ggcgcaggga ccacggtcac  cgtctcctca       420
gccaaaacga caccccatc  tgtctatcca ctggccctg  gatctgctgc  ccaaactaac       480
tccatggtga ccctgggatg cctggtcaag ggctatttcc ctgagccagt  gacagtgacc       540
tggaactctg gatccctgtc cagcggtgtg cacaccttcc cagctgtcct  gcagtctgac       600
ctctacactc tgagcagctc agtgactgtc ccctccagca cctggcccag  cgagaccgtc       660
acctgcaacg ttgcccaccc ggccagcagc accaaggtgg acaagaaaat  tgtgcccagg       720
gattgtggtt gtaagccttg catatgtaca gtcccagaag tatcatctgt  cttcatcttc       780
cccccaaagc ccaaggatgt gctcaccatt actctgactc ctaaggtcac  gtgtgttgtg       840
gtagacatca gcaaggatga tcccgaggtc cagttcagct ggtttgtaga  tgatgtggag       900
gtgcacacag ctcagacgca accccgggag gagcagttca acagcacttt  ccgctcagtc       960
agtgaacttc ccatcatgca ccaggactgg ctcaatggca aggagttcaa  atgcagggtc      1020
aacagtgcag ctttccctgc ccccatcgag aaaaccatct ccaaaaccaa  aggcagaccg      1080
aaggctccac aggtgtacac cattccacct cccaaggagc agatgccaa   ggataaagtc      1140 agtctgacct gcatgataac agacttcttc cctgaagaca ttactgtgga  gtggcagtgg      1200
aatgggcagc cagcggagaa ctacaagaac actcagccca tcatggacac  agatggctct      1260
tacttcgtct acagcaagct caatgtgcag aagagcaact gggaggcagg  aaatactttc      1320
```

```
acctgctctg tgttacatga gggcctgcac aaccaccata ctgagaagag cctctcccac   1380
tctcctggta aatga                                                    1395
```

<210> SEQ ID NO 2
<211> LENGTH: 464
<212> TYPE: PRT
<213> ORGANISM: Mus musculus

<400> SEQUENCE: 2

```
Met Tyr Leu Gly Leu Asn Tyr Val Phe Ile Val Phe Leu Leu Asn Gly
1               5                   10                  15

Val Gln Ser Glu Leu Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Lys Gly Leu
    50                  55                  60

Glu Trp Ile Ala Glu Ile Arg Ser Lys Ala Asn Asn Tyr Ala Thr Tyr
65                  70                  75                  80

Phe Ala Glu Ser Val Lys Gly Arg Phe Thr Ile Ser Arg Asp Asp Ser
                85                  90                  95

Lys Ser Gly Val Tyr Leu Gln Met Asn Asn Leu Arg Ala Glu Asp Thr
            100                 105                 110

Gly Ile Tyr Phe Cys Thr Lys Leu Ser Leu Arg Tyr Trp Phe Phe Asp
        115                 120                 125

Val Trp Gly Ala Gly Thr Thr Val Thr Val Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Asp Ile Ser Lys Asp Asp Pro
    275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365
```

Pro Pro Pro Lys Glu Gln Met Ala Lys Asp Lys Val Ser Leu Thr Cys
            370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460

<210> SEQ ID NO 3
<211> LENGTH: 363
<212> TYPE: DNA
<213> ORGANISM: Artificial sequence
<220> FEATURE:
<223> OTHER INFORMATION: nucleotide sequence for the VH of mAb 7E heavy
      chain

<400> SEQUENCE: 3
gaattgaagc ttgaggagtc tggaggaggc ttggtgcagc ctggaggatc catgaaactc      60
tcttgtgctg cctctggatt cactttagt gacgcctgga tggactgggt ccgccagtct     120
ccagagaagg ggcttgagtg gattgctgaa attagaagca agctaataa ttatgcaaca     180 tactttgctg agtctgtgaa agggaggttc accatctcaa gagatgattc caaaagtggt     240
gtctacctgc aaatgaacaa cttaagagct gaggacactg gcatttattt ctgtaccaag     300
ttatcactac gttactggtt cttcgatgtc tggggcgcag gaccacggt caccgtctcc     360 tca                                                                   363

<210> SEQ ID NO 4
<211> LENGTH: 122
<212> TYPE: PRT
<213> ORGANISM: Artificial sequence
<220> FEATURE:
<223> OTHER INFORMATION: Amino acid sequence for the VH of mAb 7E heavy
      chain

<400> SEQUENCE: 4

Ser Glu Leu Lys Leu Glu Glu Ser Gly Gly Gly Leu Val Gln Pro Gly
1               5                   10                  15

Gly Ser Met Lys Leu Ser Cys Ala Ala Ser Gly Phe Thr Phe Ser Asp
            20                  25                  30

Ala Trp Met Asp Trp Val Arg Gln Ser Pro Glu Lys Gly Leu Glu Trp
        35                  40                  45

Ile Ala Glu Ile Arg Ser Lys Ala Asn Asn Tyr Ala Thr Tyr Phe Ala
    50                  55                  60

Glu Ser Val Lys Gly Arg Phe Thr Ile Ser Arg Asp Asp Ser Lys Ser
65                  70                  75                  80

Gly Val Tyr Leu Gln Met Asn Asn Leu Arg Ala Glu Asp Thr Gly Ile
                85                  90                  95

Tyr Phe Cys Thr Lys Leu Ser Leu Arg Tyr Trp Phe Phe Asp Val Trp
            100                 105                 110

Gly Ala Gly Thr Thr Val Thr Val Ser Ser
        115                 120

```
<210> SEQ ID NO 5
<211> LENGTH: 720
<212> TYPE: DNA
<213> ORGANISM: Mus musculus

<400> SEQUENCE: 5
atgatgagtc ctgcccagtt cctgtttctg ttagtgctct ggattcggga aaccaacggt      60
gattttgtga tgacccagac tccactcact ttgtcggtta ccattggaca accagcctcc     120
atctcttgca agtcaagtca gagcctcttg gatagtgatg gaaagacata tttgaattgg     180
ttgttacaga ggccaggcca gtctccaaag cacctcatct atctggtgtc taaactggac     240
tctggagtcc ctgacaggtt cactggcagt ggatcaggga ccgatttcac actgagaatc     300
agcagagtgg aggctgagga tttgggagtt tattattgct ggcaaagtac acattttccg     360
tggacgttcg gtggaggcac caagctggaa atcaaacggg ctgatgctgc accaactgta     420
tccatcttcc caccatccag tgagcagtta acatctggag gtgcctcagt cgtgtgcttc     480
ttgaacaact tctacaagtg gaagattgat ggcagtgaac gacaaaatgg cgtcctgaac     540
agttggactg atcagcccaa agacatcaat gtcgacagca agacagcac ctacagcatg     600 agcagcaccc tcacgttgac caaggacgag tatgaacgca taacagcta tcctgtgag      660 gccactcaca agacatcaac ttcacccatt gtcaagagct tcaacaggaa tgagtgttag     720

<210> SEQ ID NO 6
<211> LENGTH: 239
<212> TYPE: PRT
<213> ORGANISM: Mus musculus

<400> SEQUENCE: 6

Met Met Ser Pro Ala Gln Phe Leu Phe Leu Leu Val Leu Trp Ile Arg
1               5                  10                  15

Glu Thr Asn Gly Asp Phe Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Arg
    50                  55                  60

Pro Gly Gln Ser Pro Lys His Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Arg Ile Ser Arg Val Glu Ala Glu Asp Leu Gly Val Tyr Tyr
            100                 105                 110

Cys Trp Gln Ser Thr His Phe Pro Trp Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220
```

```
Thr Ser Thr Ser Pro Ile Val Lys Ser Phe Asn Arg Asn Glu Cys
225                 230                 235

<210> SEQ ID NO 7
<211> LENGTH: 339
<212> TYPE: DNA
<213> ORGANISM: Artificial sequence
<220> FEATURE:
<223> OTHER INFORMATION: Nucleotide sequence of the VL of mAb 7E light
      chain

<400> SEQUENCE: 7
gattttgtga tgacccagac tccactcact ttgtcggtta ccattggaca accagcctcc      60
atctcttgca agtcaagtca gagcctcttg gatagtgatg gaaagacata tttgaattgg    120
ttgttacaga ggccaggcca gtctccaaag cacctcatct atctggtgtc taaactggac    180
tctggagtcc ctgacaggtt cactggcagt ggatcaggga ccgatttcac actgagaatc    240
agcagagtgg aggctgagga tttgggagtt tattattgct ggcaaagtac acattttccg    300
tggacgttcg gtggaggcac caagctggaa atcaaacgg                           339

<210> SEQ ID NO 8
<211> LENGTH: 114
<212> TYPE: PRT
<213> ORGANISM: Artificial sequence
<220> FEATURE:
<223> OTHER INFORMATION: Amino acid sequence of the VL of mAb 7E light
      chain

<400> SEQUENCE: 8

Gly Asp Phe Val Met Thr Gln Thr Pro Leu Thr Leu Ser Val Thr Ile
1               5                   10                  15

Gly Gln Pro Ala Ser Ile Ser Cys Lys Ser Ser Gln Ser Leu Leu Asp
            20                  25                  30

Ser Asp Gly Lys Thr Tyr Leu Asn Trp Leu Leu Gln Arg Pro Gly Gln
        35                  40                  45

Ser Pro Lys His Leu Ile Tyr Leu Val Ser Lys Leu Asp Ser Gly Val
    50                  55                  60

Pro Asp Arg Phe Thr Gly Ser Gly Ser Gly Thr Asp Phe Thr Leu Arg
65                  70                  75                  80

Ile Ser Arg Val Glu Ala Glu Asp Leu Gly Val Tyr Tyr Cys Trp Gln
                85                  90                  95

Ser Thr His Phe Pro Trp Thr Phe Gly Gly Gly Thr Lys Leu Glu Ile
            100                 105                 110

Lys Arg
```